United States Patent [19]

Kobayashi et al.

[11] Patent Number: 4,910,137

[45] Date of Patent: Mar. 20, 1990

[54] TWIG BRANCHED CYCLODEXTRIN

[75] Inventors: Shoichi Kobayashi, Tsuchiura; Mitsuru Monma; Toshiya Takano, both of Ibaraki, all of Japan

[73] Assignee: Director of National Food Research Institute, Ministry of Agriculture, Forestry and Fisheries, Ibaraki, Japan

[21] Appl. No.: 946,697

[22] Filed: Dec. 24, 1986

[30] Foreign Application Priority Data

Aug. 13, 1986 [JP] Japan ................................. 61-188641

[51] Int. Cl.[4] ...................... C12P 19/44; C12P 19/18; C12P 19/08
[52] U.S. Cl. ........................................ 435/74; 435/95; 435/97; 435/99; 435/101; 435/103; 536/103
[58] Field of Search ...................................... 435/95–98, 435/74, 103, 101; 536/103

[56] References Cited

U.S. PATENT DOCUMENTS 4,384,898 5/1983 Okada et al. ........................... 435/99
4,668,626 5/1987 Kobayashi et al. .................... 435/95

*Primary Examiner*—Herbert J. Lilling
*Attorney, Agent, or Firm*—Frishauf, Holtz, Goodman & Woodward

[57] ABSTRACT

When an enzymatic reaction is performed in a reaction mixture containing cyclodextrin and a branched maltooligosaccharide or a saccharide mixture of the same in the presence of a branch-splitting enzyme such as pullulanase, a twig branched cyclodextrin, i.e. a branched cyclodextrin of which the branched portion is formed of a moiety of a branched maltooligosaccharide, is formed. This product is a novel compound not known in the prior art and is a useful material in various industrial fields such as foods, cosmetics, medicines and the like by virtue of the unique properties of, for example, clathrate formation and complex formation with atoms or ions of metals.

11 Claims, 1 Drawing Sheet

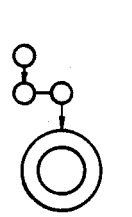 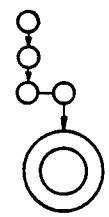 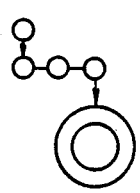
FIG.1A    FIG.1B    FIG.1C
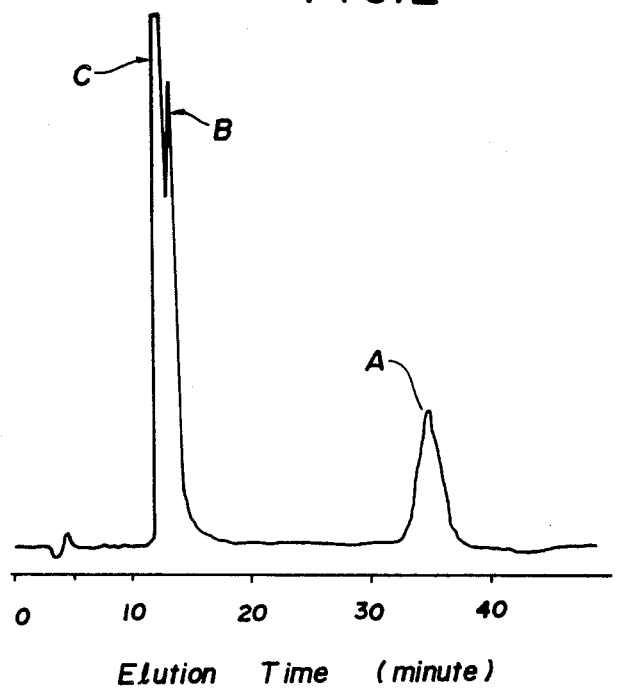
FIG.2

TWIG BRANCHED CYCLODEXTRIN

BACKGROUND OF THE INVENTION

The present invention relates to a twig branched cyclodextrin (branched dextrin branched cyclodextrin, hereinafter abbreviates as "BB-CD") and a method for the preparation thereof or, more particularly, to a BB-CD of which the branched portion is formed of a moiety of branched maltooligosaccharide and an efficient method for the preparation thereof.

Branched cyclodextrins have excellent and useful properties of, for example, high solubility in water so that investigations have been hitherto undertaken intensively for the development of the method for the preparation as well as utilization of such branched cyclodextrins. Several variations of branched cyclodextrins are known including those of which the branched portion is formed of a moiety of α-1,4glucan such as glucose, maltose and the like. These branched cyclodextrins are prepared enigmatically either by utilizing a specific enzyme having activity of synthesis of a branched cyclodextrin or by the enzymatic reaction in a mixture of cyclodextrin and an α-1,4-glucan such as maltose and maltotriose in the presence of a branch-splitting enzyme.

Branched cyclodextrins of which the branched portion is formed of a maltosyl or higher group are converted into a glucosyl cyclodextrin in the presence of glucoamylase or α-amylase since the branched portion is susceptible to the attack of these enzymes. Accordingly, it is eagerly desired to develop a branched cyclodextrin of which the branched portion is insusceptible to these enzymes.

It has been recently reported that panose can be used as the branched portion in the preparation of certain metal complexes having stability, and metals such as zinc, calcium and the like or ions thereof are expected to form a stable complex in the simultaneous presence of a branched dextrin such as panose and cyclodextrin. The complex formation of metals can be performed by the combined use of a branched dextrin and cyclodextrin but a alternative method is to use a BB-CD as a combination of a branched dextrin such as panose and cyclodextrin as a possibility. Such a cyclodextrin derivative, however, is not known in the prior art so that the above mentioned possibility seemed to be far from reality. Much less, no method has been reported for the preparation of such a cyclodextrin derivative.

For example, a method for the preparation of a branched cyclodextrin is known on the base of the discovery that maltosyl-and maltotriosyl-cyclodextrins are formed from cyclodextrin and maltose or maltotriose by utilizing the reverse reaction of a branch-splitting enzyme such as pullulanase. It is not known, however, that a BB-CD is formed from a branched dextrin and cyclodextrin by the reverse reaction of the branch-splitting enzyme.

SUMMARY OF THE INVENTION

An object of the present invention is to provide a twig branched cyclodextrin which is a novel compound not known in the prior art nor described in any literatures.

Another object of the invention is to provide a method for the preparation of the above mentioned BB-CD by utilizing an enzymatic reaction.

Thus, the BB-CD provided by the invention as a novel compound is a branched cyclodextrin of which the branched portion is formed of a moiety of a branched maltooligosaccharide.

The above mentioned BB-CD can be prepared by the enzymatic reaction of cyclodextrin and a branched maltooligosaccharide or a saccharide mixture containing the same in the presence of a branch-spitting enzyme.

BRIEF DESCRIPTION OF THE DRAWING

FIG. 1(a)-(c) show, the structures of typical twig branched cyclodextrins, of which 1(a), 1(b) and 1(c), II and III are for panosyl cyclodextrin, $6^2$-α-isomaltosylmaltosyl cyclodextrin and $6^3$-α-glucosylmaltotriosyl cyclodextrin, respectively. The marks of a single circle, double circle, horizontal line and vertical line with arrow indicate a glucose residue, cyclodextrin, α-1,4-linkage and α-1,6-linkage, respectively.

FIG. 2 shows an elution curve of the panosyl α-cyclodextrin formed from panose and α-cyclodextrin. In the figure, A, B and C are for panosyl cyclodextrin, α-cyclodextrin and panose, respectively.

DETAILED DESCRIPTION OF THE PREFERRED EMBODIMENTS

The inventors have continued extensive investigations with the above described object and arrived at a discovery that a BB-CD is formed from cyclodextrin and a branched dextrin by the reverse reaction in the presence of a branch-splitting enzyme when the reaction is continued so far. Namely, it has been unexpectedly discovered that a BB-CD having a moiety of branched dextrin as the branch is formed when cyclodextrin and a branched dextrin such as panose, α-amylase-limited dextrin and the like are mixed together and reacted in the presence of a branch-splitting enzyme and completed the present invention on the base of this discovery.

The BB-D here implied is a branched cyclodextrin having a specific structure of which the branched portion is formed of a moiety of branched maltooligosaccharide. A twig branched cyclodextrin, in which a molecule of a branched maltooligosaccharide is bonded to the molecule of cyclodextrin, is formed when cyclodextrin and a branched maltooligosaccharide such as panose, i.e. $6^2$-α-glucosyl maltose, $6^3$-α-glucosyl maltotriose and the like are mixed together and reacted in the presence of a branch-splitting enzyme.

The branched portion of the BB-CD may be formed of a variety of moieties including $6^2$-α-glucosyl maltose, $6^2$-α-isomaltosyl maltose, $6^3$-α-glucosyl maltotriose, $6^3$-α-glucosyl maltotetraose, $6^4$-α-glucosyl maltotetraose and the like.

The reaction conditions should be selected so as to maximize the yield of the BB-CD. In an example, panose and α-cyclodextrin were dissolved each in a final concentration of 56% and 14%, respectively, and the substrate solution was admixed with a commercially available enzyme of pullulanase in an amount of 80 IU per g of the total amount of the two substrate materials so that a BB-CD was obtained in a yield of 20 to 40% after 3 to 7 days of reaction under a temperature of 40°-70° C. The BB-CD as the product was examined for the chemical structure by an enzymatic reaction in the presence of a branch-splitting enzyme in a solution of a relatively low concentration of 5% or lower followed by the analysis of the reaction product by high-performance liquid chromatography and paper chromatography. The results of analysis indicated that the reaction product contained cyclodextrin and the branched maltooligosaccharide in a molar ratio of 1:1 leading to a conclusion that the BB-CD was formed of a molecule of the branched maltooligosaccharide bonded to a cyclodextrin ring through an α-1,6-linkage.

As a further possibility, use of a differently active enzyme in place of pullulanase may produce a dually branched cyclodextrin having two or more branched portions formed of two or more molecules of branched dextrin.

The branched oligosaccharide forming the branches on the cyclodextrin rings by the enzymatic activity of the branchsplitting enzyme is not particularly limitative provided that the saccharide backbone has an α-1,4-glucan chain higher degree of polymerization than maltosyl bonded thereto and the branch is bonded to the glucose residue other than that of the reducing end. Namely, molecules of panosyl panose and $6^2$-α-maltosylmaltose may be bonded to the cyclodextrin ring as the branch thereto at least partly although they are susceptible to the enzymolytic decomposition by a branchsplitting enzyme. The BB-CD here implied includes a cyclodextrin having two or more of α-1,6-linkages in the branched portions formed of the branched maltooligosaccharide, which is referred to as a multiply branched dextrin branched cyclodextrin.

The above given discussion may lead to a presumption that the branch-forming saccharide in general should have a structure symbolically expressed by-●●, in which ○ denotes a glucose residue and ⊘ denotes a reduced end bonded together through an α-1,4-linkage expressed by the horizontal line. The portion expressed by the broken line is not particularly limitative with respect to the saccharide composition and the type of the linkage bonding the glucose units. Further, it would be also a fair presumption that the saccharide may have a hyroxyethyl group, carboxymethyl group, phosphate group, acetyl group and the like bonded to the inherent saccharide structure. Thus, the method of the present invention would be applicable to the preparation of various kinds of branched cyclodextrin derivatives.

The branch-splitting enzyme usable in the method of the present invention includes pullulanase, isoamylase and the like obtained as a microbial product of various microorganisms and selection should be made depending on the length of the saccharide backbone of the brance-forming branched maltooligosaccharide. Pullulanase is preferred usually when the branches should be formed of a branched maltooliosaccharide having a saccharide backbone of a relatively small length while either one of pullulanase and isoamylase can be used when the branch-forming branched maltoolgosaccharide has a relatively long sacchride backbone.

A preferable source of he branched maltooligosaccharide is panose and a high efficiency of the inventive method is obtained by using the panose formed at an early stage of the enzymatic reaction of maltose in a high concentration by the enzymatic activity of glucoamylase or transglucosidase. $6^3$-α-Glucosyl maltotriose is produced in large quantities from pullulan by the enzymatic reaction of an enzyme mixture of pullulanase and glucoamylase and $6^3$-α-glucosyl maltotriose and $6^3$-α-glucosyl maltotetraose are produced by the enzymatic reaction from amylopectin or the starch of glutinous corn as the limiting dextrin thereof under strong reaction conditions of α-amylase. Further, it would be probable that various kinds of branched maltooligosaccharides can be produced by the reverse reaction of isopullulanase from a mixture of isomaltose with glucose, maltose or maltotriose.

When panose is subjected to an enzymatic reaction in a high concentration with pullulanase, for example, the reaction product is panosyl panose which in turn should be enzymolytically decomposed into isomaltose and isomaltosyl maltose by the enzymatic activity of isopullulanase.

$6^2$-α-Isomaltosyl maltose can be obtained as a fraction of glucose tetramer by the enzymatic treatment of maltosyl panose which is obtained from maltose and panose by the reaction of reverse synthesis with pullulanase, with glucoamylase.

The starting material for the preparation of the inventive twig branched cyclodextrin prepared in the above described manner includes products at various stages of purification from the reaction mixture as such after the reaction containing glucose, maltose and the like to a branched dextrin after full purification.

The cyclodextrin as the starting material of the inventive method includes α-, β- and γ-cyclodextrins either singly as isolated or as a mixture as well as mixtures thereof with oligosaccharides such as glucose, maltose and the like. When the starting material also contains a longchain oligosaccharide higher than maltose and/or dextrin, the branch-forming reaction should be performed by adding β-amylase to the reaction mixture.

Although the BB-CD of the invention can be obtained from various kinds of starting materials, the content of the desired product in the reaction mixture after the enzymatic reaction depends on the kind of the starting material and the yield of the branched cyclodextrin may differ depending o the content of maltooligosaccharides other than glucose and isomaltose. Accordingly, the saccharide solution used in the enzymatic reaction should contain the objective branched cyclodextrin in an as large as possible amount in order to obtain the BB-CD in a high yield. It is preferable that the saccharide solution used in the enzymatic reaction should be upgraded in advance in respect of the content of the branched cyclodextrin, for example, by precipitating the trisaccharides and higher saccharides with an organic solvent such as acetone, ethyl alcohol and the like added to the solution so as to increase the relative content of the branched cyclodextrin, by removing the disaccharides and glucose by using yeast to assimilate them or by separating the branched cyclodextrin with a column chromatographic procedure.

As is described above, the present invention provides an efficient method for the preparation of various kinds of BB-CD as a class of novel compounds. They are useful as a base of medicaments since the branched portion of these cyclodextrin derivatives is insusceptible to or highly resistant against the enzymatic activity of α-amylase and glucoamylase. Furthermore, they have a possibility as a novel base material widely utilizable in various industrial fields of foods, cosmetics and so on since the synergistic combination of the branched portion and the central cavity of the cyclodextrin ring would greatly increase the clathrate effect inherent to the cyclodextrin.

In particular, the BB-CD is still less digestive than conventional cyclodextrins and promising as an additive in healthful or special foods for the prevention of fatness or as a proliferation factor of bifidus bacteria. Further, the BB-CD itself may have a physiological activity by virtue of the specific structure and a strong physiological activity may be exhibited as a result of clathrate formation with atoms or ions of metal.

Various methods for the preparation of the BB-CD may give a product containing the same in a different concentration as well as the cyclodextrin, branched dextrin, glucose, maltose and the like used as the starting materials.

When a high purity is desired of the BB-CD, the reaction mixture after the enzymatic reaction may be purified by a conventional method such as column chromatography, fractional precipitation with solvents and the like.

In the following, examples are given to illustrate the present invention in more detail.

EXAMPLE 1

A reaction mixture was prepared by dissolving 2.8 grams (g) of panose prepared by the inventors and 0.7 g of α-cyclodextrin in 4 ml of water followed by the addition of 1 ml of a commercially available pullulanase solution (200 pun/g, a product by Novo Co.) and adjustment of the pH at 5.0. The enzymatic reaction was performed in the thus prepared reaction mixture at 60° C. for 7 days to obtain panosyl-α-cyclodextrin in a yield of 42%.

The determination of the product was performed by highperformance liquid chromatography using a column filled with a silica gel powder (Unisil-NH$_2$, average particle diameter 5 μm) loaded with 3 μl of the reaction mixture and 60% acetonitrile as the eluant at a flow rate of 1 ml/minute.

EXAMPLE 2

The experimental procedure was substantially the same as in Example 1 excepting replacement of α-cyclodextrin with β-cyclodextrin to give panosyl-β-cyclodextrin at a yield of 37%.

EXAMPLE 3

The experimental procedure was substantially the same as in Example 1 excepting replacement of α-cyclodextrin with γ-cyclodextrin to give panosyl-γ-cyclodextrin at a yield of 48%.

EXAMPLE 4

An enzymatic reaction of maltose in an aqueous solution with addition of a commercially available product of transglucosidase gave a saccharide solution containing a saccharide mixture composed of 26% o glucose, 28% of maltose, 7% of isomaltose, 33 of panose, 4% of maltotriose and 2% of isomaltotriose. After adjustment of the saccharide concentration to 80%, the saccharide solution was admixed with α-cyclodextrin in an amount of 25% of the overall amount of the saccharides and a commercially available product of pullulanase in an amount of 100 IU per g of the saccharides in the solution. The enzymatic reaction wa performed in the same manner as in Example 1 to give panosyl-α-cyclodextrin as the product, of which the conversion from the α-cyclodextrin added to the reaction mixture was 13%. The reaction mixture as such could be used in some applications without further purification.

EXAMPLE 5

Starch of glutinous Indian corn was enzymatically liquefied at 37° C. using a heat-resistant amylase (Chrystase, a product by Daiwa Kasei Co., 3000–4000 IU/g) into a saccharide solution, of which the concentration of the saccharide was adjusted to 75%. The solution was further admixed with the same enzyme as above in an amount of 400 milligrams (mg) per g of the substrate followed by the adjustment of the final concentration of the substrate to 10% and the pH to 5.0. The enzymatic reaction was performed in the thus prepared reaction mixture at 60° C. for 7 days to give a limiting dextrin in a yield of 12.8%.

The reaction mixture after the reaction was admixed with 3.5 times by volume of acetone to give a saccharide mixture composed of 11%, 29%, 5%, 31% and 25% of glucose, maltose, maltotrios, $6^3$-60-glucosyl maltotriose and other branched cyclodextrins, respectively as a precipitate.

The thus obtained saccharide mixture was admixed with α-cyclodextrin in an amount of 25% of the overall amount of the saccharide therein followed by the adjustment of the saccharide concentration to 70% and addition of a commercially available product of pullulanase in an amount of 100 IU per g of the saccharides. The enzymatic reaction in this reaction mixture was performed in the same manner as in Example 1 to give $6^3$-α-glucosyl maltotriosyl-α-cyclodextrin As teh product of which the conversion from α-cyclodextrin was 10%.

EXAMPLE 6

A reaction mixture was prepared using the same substrate as in Example 5 with addition of a commercially available product of isoamylase in an amount of 1000 IU per g of the overall amount of the saccharides followed by the adjustment of the pH to 3.8. The enzymatic reaction in this reaction mixture was performed at 40° C. for 2 days to give $6^3$-α-glucosyl maltotriose and a twig branched cyclodextrin having a branch of a branched dextrin moiety of a molecule larger than the same.

What is claimed is:

1. A twig branched cyclodextrin having a branched portion formed of a moiety of branched maltooligosaccharide.

2. A twig branched cyclodextrin wherein the branched portion of the branched cyclodextrin is formed of a moiety of a branched maltooligosaccharide selected from the group consisting of $6^2$-α-glucosyl maltose, $6^2$-α-isomaltosyl maltose, $6^3$-α-glucosyl maltotriose, $6^3$-α-glucosyl maltotetraose and $6^4$-α-glucosyl maltotetraose.

3. The twig branched cyclodextrin as claimed in claim 1 wherein the ring portion of the cyclodextrin has a structure of α-, β- or γ-cyclodextrin.

4. A twig branched cyclodextrin wherein the branched portion of the branched cyclodextrin is formed of a moiety of a branched maltooligosaccharide selected from the group consisting of $6^2$-alpha-glucosyl maltose, $6^2$-alpha-isomaltosyl maltose, $6^3$alpha-glucosyl maltotriose, $6^3$-alpha-glucosyl maltotetraose and $6^4$-alpha-glucosyl maltotetraose and the ring portion of the cyclodextrin has a structure of alpha-, beta-, or gamma-cyclodextrin.

5. A twig branched cyclodextrin designated panosyl cyclodextrin.

6. A twin branched cyclodextrin designated panosyl-alpha-cyclodextrin.

7. A twig branched cyclodextrin designated panosyl-beta-cyclodextrin.

8. A twig branched cyclodextrin designated panosyl-gamma-cyclodextrin.

9. The twig branched cyclodextrin as claimed in claim 1 designated $6^2$-alpha-isomaltosyl cyclodextrin.

10. The twig branched cyclodextrin as claimed in claim 1 designated $6^3$-alpha-glucosylmaltotriosyl cyclodextrin.

11. The twig branched cyclodextrin as claimed in claim 1 designated $6^3$-alpha-glucosylmaltotriosyl-alpha-cyclodextrin.

* * * * *